US010035011B2

(12) United States Patent
Gittard (10) Patent No.: US 10,035,011 B2
(45) Date of Patent: Jul. 31, 2018

(54) CATHETER ATTACHMENT MECHANISM (71) Applicant: Cook Medical Technologies LLC, Bloomington, IN (US)

(72) Inventor: Shaun D. Gittard, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 143 days.

(21) Appl. No.: 14/209,637

(22) Filed: Mar. 13, 2014

(65) Prior Publication Data
US 2014/0276652 A1 Sep. 18, 2014

Related U.S. Application Data (60) Provisional application No. 61/800,190, filed on Mar. 15, 2013, provisional application No. 61/857,505, filed on Jul. 23, 2013.

(51) Int. Cl.
*A61M 25/18* (2006.01)
*A61M 39/10* (2006.01)
A61M 25/00 (2006.01)

(52) U.S. Cl.
CPC ..... *A61M 39/1011* (2013.01); *A61M 25/0097* (2013.01); *A61M 2039/1027* (2013.01); *Y10T 29/49826* (2015.01)

(58) Field of Classification Search
CPC ...... A61M 39/1011; A61M 2039/1027; A61M 25/0097; A61M 2025/0098; A61M 39/12; A61M 39/10; A61M 2039/1077
See application file for complete search history.

(56) References Cited

U.S. PATENT DOCUMENTS

| 2003/0006610 | A1* | 1/2003 | Werth | F16L 33/225 285/243 |
| 2003/0193190 | A1* | 10/2003 | Werth | F16L 33/225 285/243 |
| 2008/0009832 | A1* | 1/2008 | Barron | A61M 25/0014 604/533 |
| 2010/0013215 | A1* | 1/2010 | Werth | F16L 33/2071 285/243 |

\* cited by examiner

*Primary Examiner* — Emily Schmidt
(74) *Attorney, Agent, or Firm* — Brinks Gilson & Lione (57) ABSTRACT

The disclosure provides an apparatus and methods for securing a medical catheter. The apparatus includes a tube wall that defines a lumen extending longitudinally there through. The tube wall comprising: a plurality of flexible fingers extending along a portion of the tube wall, a longitudinal slot disposed between each pair of adjacent fingers, each of the fingers comprising an exterior surface and an interior surface. An outer protrusion extends outwardly from the exterior surface of each finger. An inner protrusion extends inwardly from the interior surface of each finger. The inner protrusions are configured to frictionally engage an outer surface of the medical catheter disposed within the lumen when the plurality of flexible fingers are moved inwardly in response to an external force applied to the outer protrusions.

19 Claims, 14 Drawing Sheets

CATHETER ATTACHMENT MECHANISM

CROSS-REFERENCES TO RELATED APPLICATIONS

This application claims the benefit of U.S. Provisional Patent Application No. 61/800,190, filed on Mar. 15, 2013, and U.S. Provisional Patent Application No. 61/857,505, filed on Jul. 23, 2013, which are hereby incorporated herein by reference in their entireties.

BACKGROUND

The present disclosure relates generally to a device for securing a medical catheter. More specifically, the disclosure relates to a device configured for connecting two medical catheters or two parts of a medical catheter.

SUMMARY

The present disclosure provides a catheter apparatus for securing a medical catheter.

One embodiment of the device includes a tubular member comprising a tube wall that defines a lumen extending longitudinally there through, the tube wall comprising: a plurality of flexible fingers extending along a portion of the tube wall, a longitudinal slot disposed between each pair of adjacent fingers, each of the fingers comprising an exterior surface and an interior surface. An outer protrusion extends outwardly from the exterior surface of each finger. An inner protrusion extends inwardly from the interior surface of each finger. The inner protrusions are configured to frictionally engage an outer surface of the medical catheter disposed within the lumen when the plurality of fingers are moved inwardly in response to an external force applied to the outer protrusions.

In a second embodiment, the device includes a first component to be inserted into a mating component. The first component includes a tubular member comprising a tube wall that defines a lumen extending longitudinally there through. The tube wall includes: a plurality of fingers extending along a portion of the tube wall, a longitudinal slot disposed between each pair of adjacent fingers. Each of the fingers includes an exterior surface and an interior surface. An outer protrusion extends outwardly from the exterior surface of each finger and an inner protrusion extends inwardly from the interior surface of each finger. The mating component includes an inner diameter less than an outer diameter of the outer protrusion. The inner protrusions are configured to frictionally engage an outer surface of the medical catheter disposed within the lumen when the mating component applies an external force to the plurality of outer protrusions and moves the flexible fingers inwardly.

In another aspect of the present invention, there is provided a method for securing a medical catheter, the method comprising: providing an apparatus comprising a tubular member comprising a tube wall that defines a lumen extending longitudinally there through, the tube wall comprising: a plurality of flexible fingers extending along a portion of the tube wall, a longitudinal slot disposed between each pair of adjacent fingers, each of the fingers comprising an exterior surface and an interior surface; the apparatus further comprising: an outer protrusion extending outwardly from the exterior surface of each finger; and an inner protrusion extending inwardly from the interior surface of each finger; inserting at least a portion of the medical catheter into the lumen; inserting the tubular member and the medical catheter into a mating component having an inner diameter less than an outer diameter of the outer protrusion; and frictionally engaging an outer surface of the inserted portion of the medical catheter with the inner protrusions when the plurality of flexible fingers are moved inwardly in response to an external force applied by the mating component to the outer protrusions.

BRIEF DESCRIPTION OF THE DRAWINGS

The disclosure can be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

DETAILED DESCRIPTION OF THE PREFERRED EMBODIMENTS

In the present application, the term "proximal" refers to a direction that is generally toward a physician during a medical procedure, while the term "distal" refers to a direction that is generally toward a target site within a patient's anatomy during a medical procedure.

Referring now to FIGS. 1-6, a first embodiment of the apparatus 100 for securing an elongate medical catheter. The apparatus 100 includes a first tubular member 110 connected with a second tubular member 102. The first tubular member 110 includes a tube wall 120 that defines a lumen 130 extending longitudinally there through. The tube wall 120 includes a plurality of flexible fingers: 122. The tubular member 110 may be affixed to a handle. The lumen 130 has an inner diameter between about 1.0 mm and 20.0 mm. The apparatus 100 is made of at least one of metal and plastic material.

The flexible fingers 122 extend along a portion 123 of the tube wall 120. There is a longitudinal slot disposed between each pair of adjacent fingers 122. For example, in FIG. 4, a longitudinal slot 124 is disposed between the pair of adjacent fingers 122. Each of the flexible fingers 122 includes an exterior surface 126 and an interior surface 128. The tubular member 110 may be affixed to a handle.

On each finger, there is an outer protrusion 132 extending outwardly from the exterior surface 126 of the finger. Each finger 122 may include multiple outer protrusions. The outer protrusion 132 may comprise at least one of the following: a tab, a ridge, a tooth, an arch, or any component protrudes outwards from the outer surface. The plurality of outer protrusions may comprise at least two tabs extending parallel to the longitudinal slot.

Figure 1:
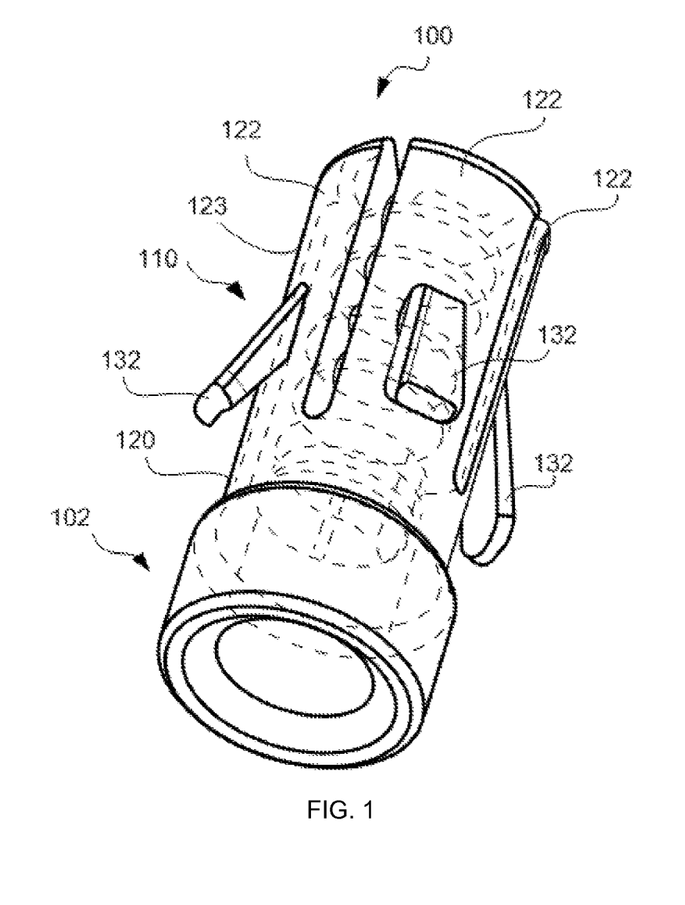
FIGS. 1-6 illustrate different views of an embodiment of the device.
Figure 2:
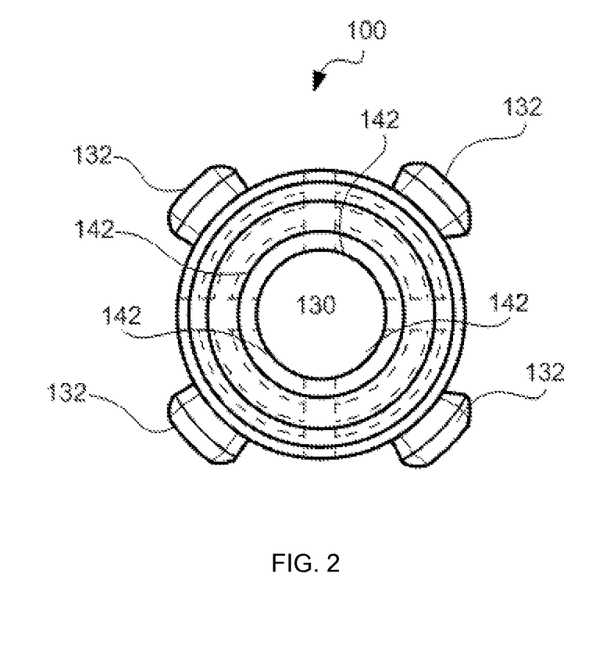
Figure 3:
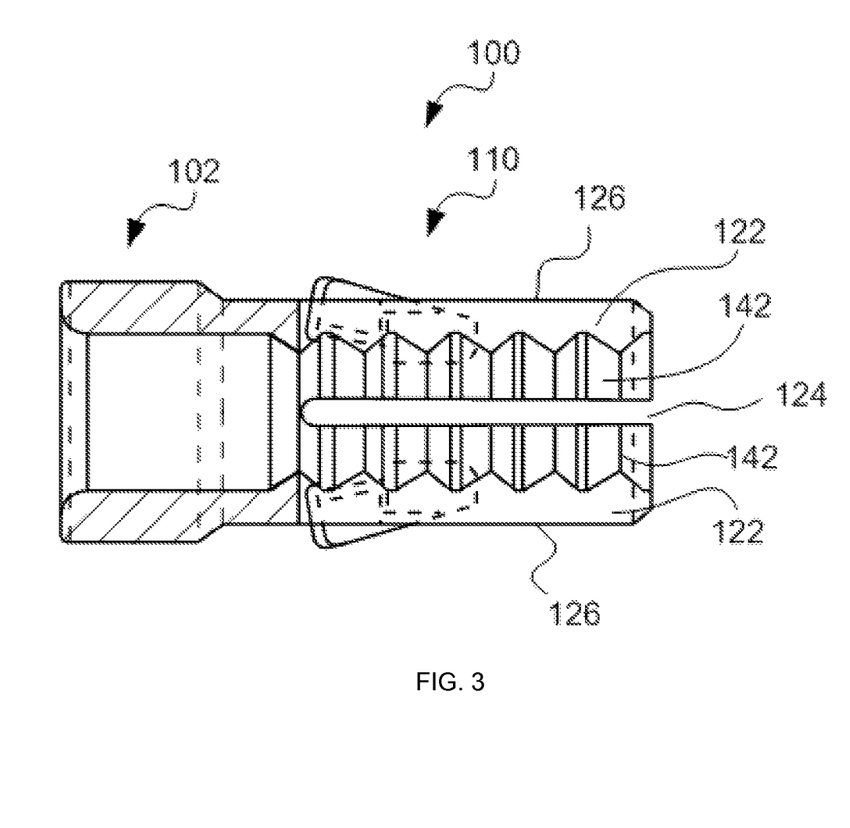
Figure 4:
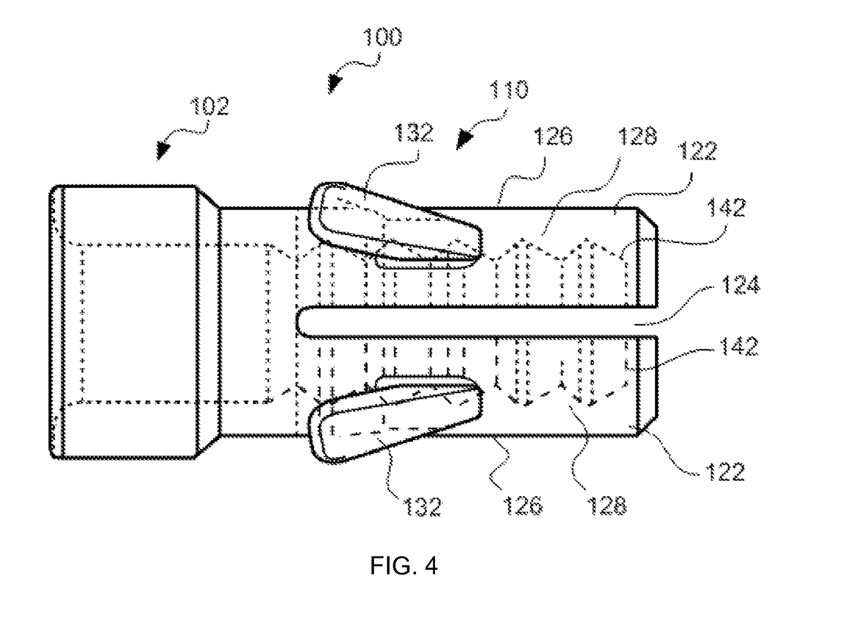

On each finger, there is an inner protrusion 142 extending inwardly from the interior surface 128 of the finger. Each finger 122 may include multiple inner protrusions. FIG. 2 shows that there are four inner protrusions 142. In FIG. 4, the inner protrusions 142 extend inwardly from the interior surface 128. The inner protrusion 142 may comprise at least one of the following: a tab, a ridge, a tooth, an arch, or any component protrudes inwards from the inner surface. The plurality of inner protrusions 142 are configured to frictionally engage an outer surface of the medical catheter disposed within the lumen 130 when the plurality of flexible fingers 122 are moved inwardly in response to an external force applied to the plurality of outer protrusions 132. The plurality of inner protrusion may comprise at least two teeth extending perpendicular to the longitudinal slot.

The embodiment shown in FIGS. 1-6 is for illustration only. The number of fingers 122 may be different and the shape of the fingers 122 may be non-linear. Similarly, the number of outer protrusions 132 and the number of inner protrusions 142 may be different. The shape of outer protrusions 132 and inner protrusions 142 may be adjusted to accommodate the surfaces of the other medical devices. Preferably, the apparatus 100 includes at least three fingers, more preferably the apparatus 100 includes three to eight fingers. The size of the fingers 122 depend on the dimensions of the medical devices that connects to the apparatus and the materials that are used. The fingers 122 are configured to be long enough and flexible enough so that the fingers 122 will bend instead of fracture when forces are applied to the fingers 122 from the exterior surface 126 or the interior surface 128.

Figure 5:
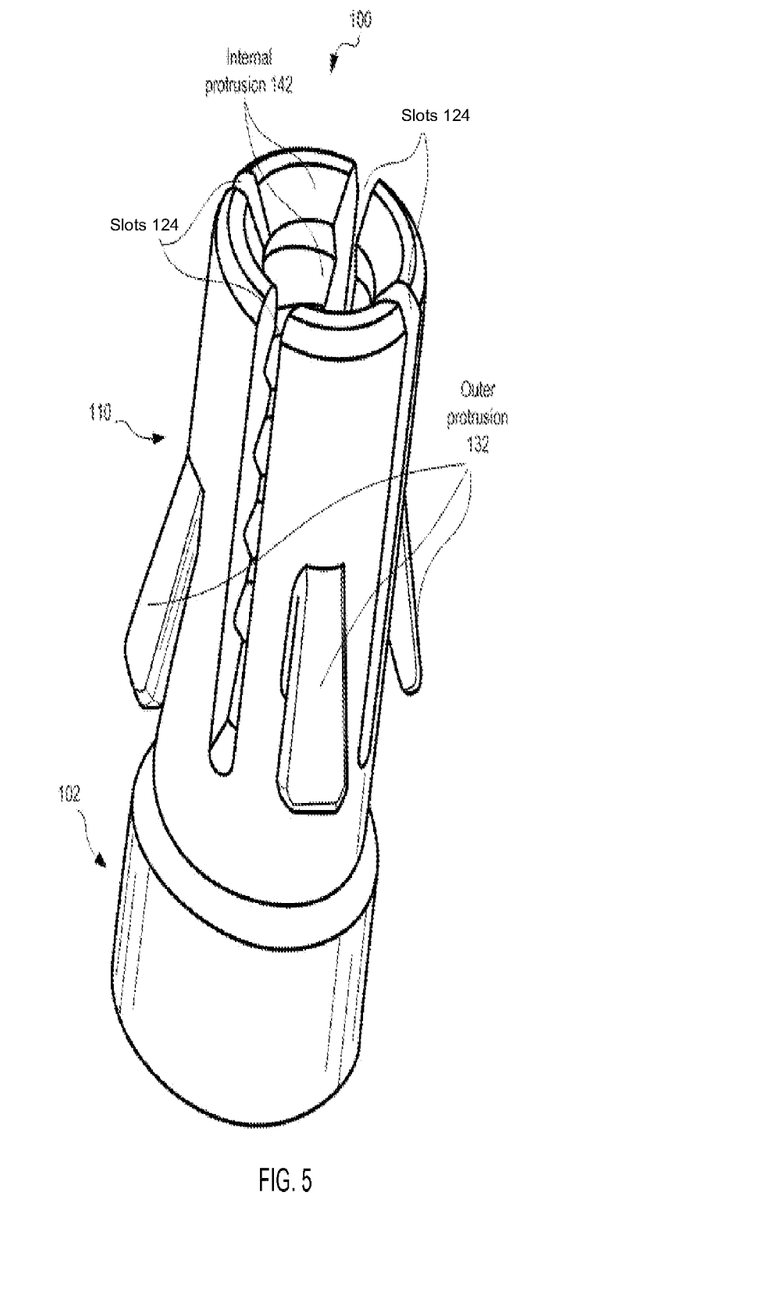

FIG. 5 shows a 3-dimensional view of a component 100 in the device. The component 100 includes four slots 124. Each slot 124 is between a pair of adjacent fingers as illustrated in FIGS. 1-4. There is an outer protrusion on the outer surface of each finger. There are also inner protrusions on the inner surface of each finger. The shape of the outer protrusions and inner protrusions are for illustration only and may be different based on the application.

Figure 6:
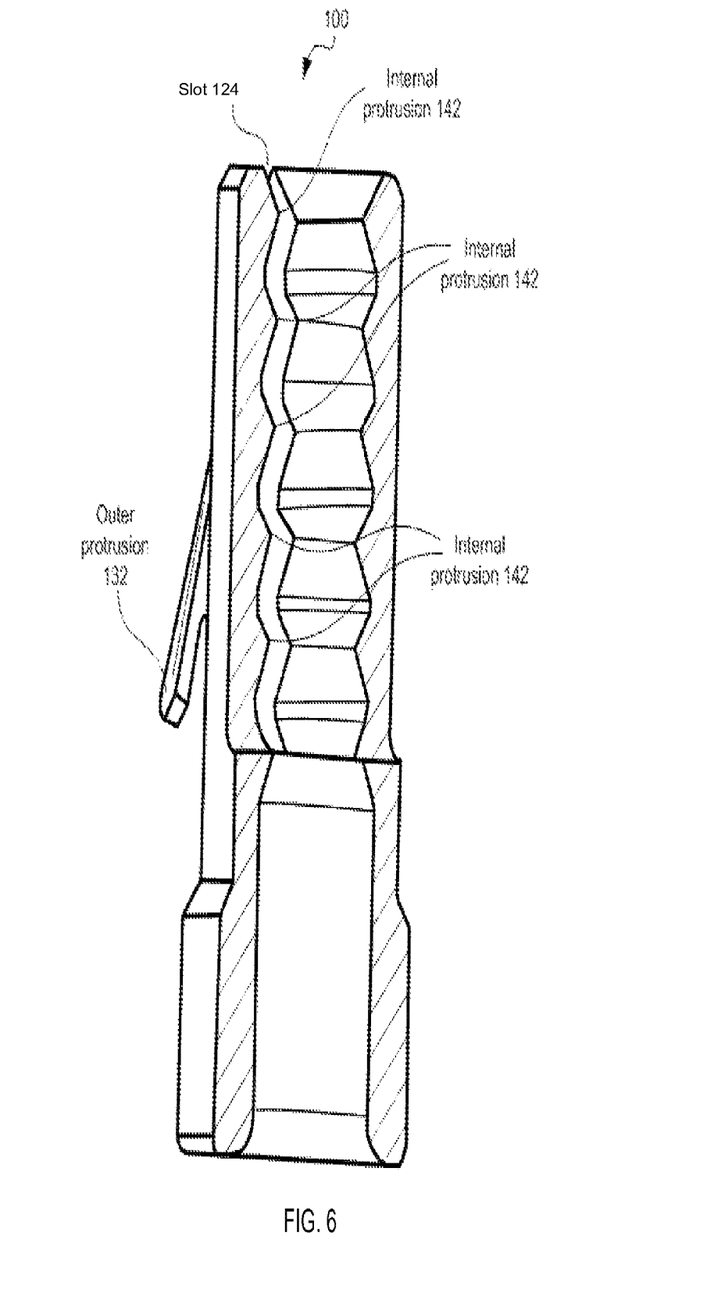

FIG. 6 shows a partial cut-through view of the component 100. There are a plurality of inner protrusions on the inner surface of the finger. The inner protrusion includes at least one of the following: a tab, a ridge, a tooth, an arch, or any component protrudes inwards from the inner surface.

Figure 7:
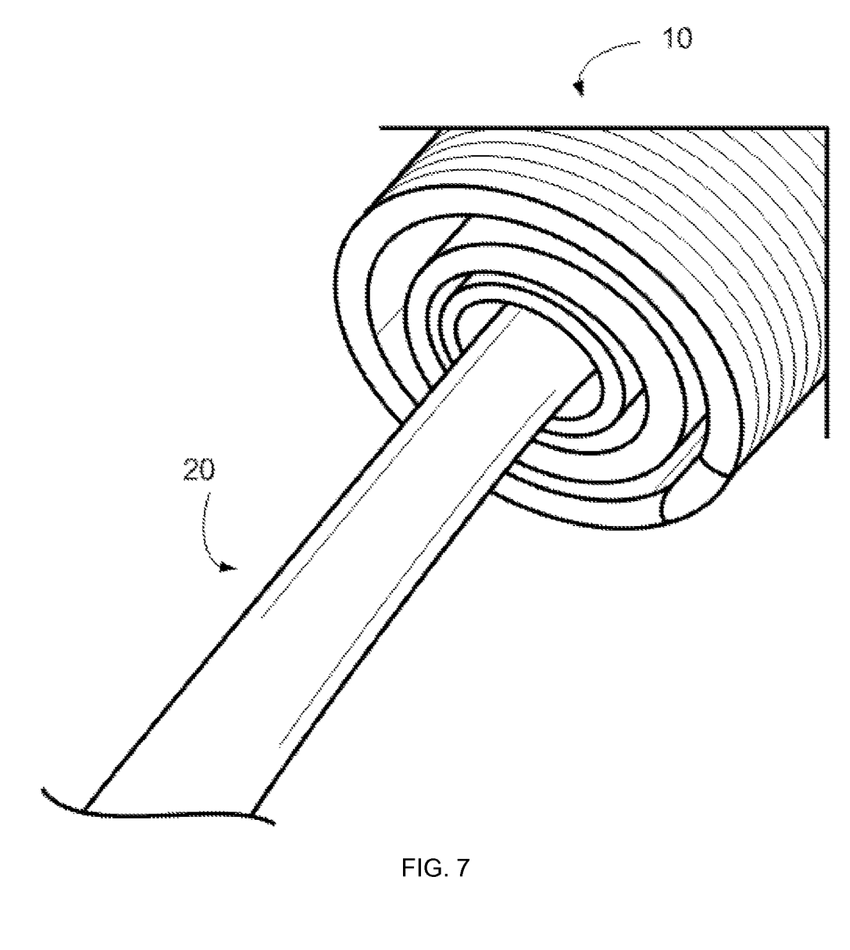
FIG. 7 illustrates a device securing a medical catheter.
Figure 8:
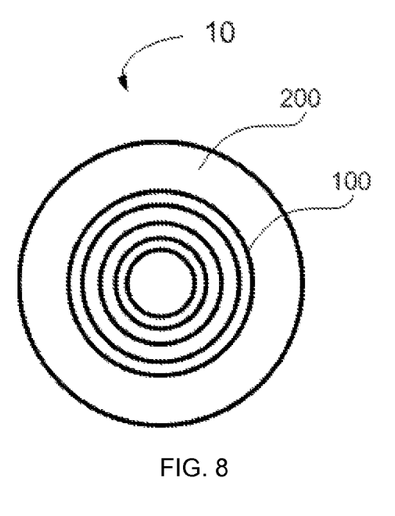
FIGS. 8-13 illustrate different views of an embodiment of the device.
Figure 9:
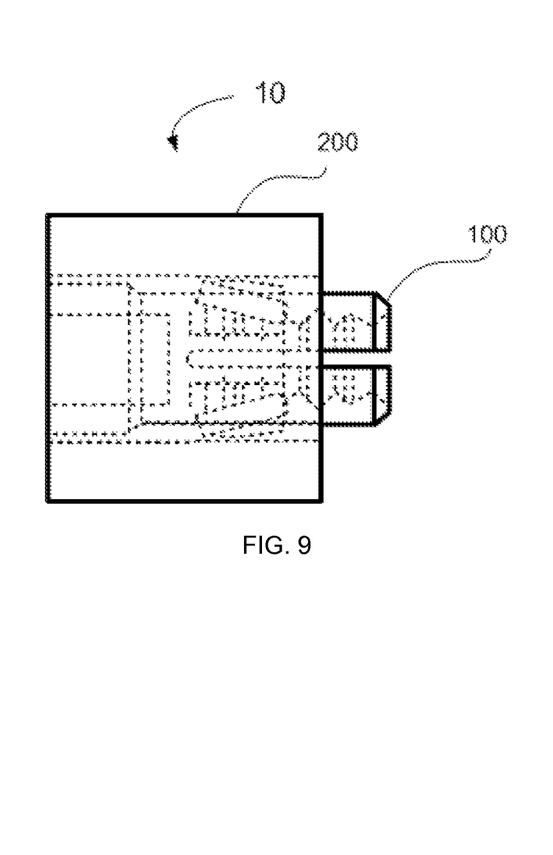
Figure 10:
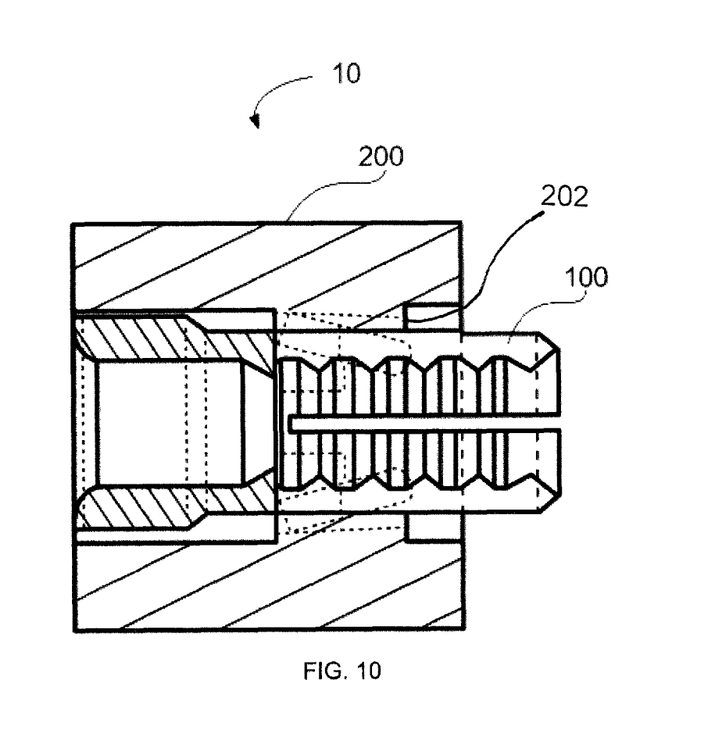

The disclosed device may be configured to attach a catheter to a component. For example, FIG. 7 shows that the device 100 attaches a catheter 20. The device 100 includes a component illustrated in FIGS. 1-6. The inner diameter of the device 10 is slightly larger than the outer diameter of the catheter 20. With the inner protrusions, the device 100 is configured to attach the catheter 20.

The disclosed device includes a cylindrical tube (component 1) in FIG. 5, with slots cut out on one end to create flexing members (fingers). These flexing members contain barbs or other teeth like protrusions on the luminal face and outward facing tabs on their outer face in FIG. 6. A medical device such as a catheter may be inserted into this cylindrical tube. Upon inserting this tube with catheter into the mating component (component 2) with an inner diameter that is smaller than the outer diameter (OD) of the tabs, the tabs will compress. Compression of the tabs results in the flexing members pressing against the catheter and the protrusions sinking into the catheter, thus achieving fixation of the catheter within component 1. A shoulder within component 2 will prevent component 1 from slipping out of place. Thus, the component 1 is configured to grip the catheter and lock into the mating component.

FIGS. 8-13 illustrate different views of a third embodiment of a device 10. In FIGS. 8-13, the device 10 includes a tube component 100 locked in a mating component 200 having an inner diameter less than an outer diameter of the outer protrusion of the tube component 100. The mating component 200 is configured to apply the external force on the plurality of plurality of outer protrusions when attached to the tube component 100. The mating component 200 may include a collar structure. The mating component 200 may have other shapes or mechanisms to lock the tube component 100. The material of the mating component 200 may be the same as the tube component 100.

Nearly all catheter-based devices require a mechanism of fixing the catheter to other components, such as handles, hubs, ports, etc. Current mechanisms for attaching a catheter to these components include overmolding, gluing, press-fitting, and friction fitting (e.g. with shrinkwrap). Attachment of catheters with lumens, especially multiple lumens, can be even more challenging as the lumens could become occluded during overmolding or gluing. Likewise, friction or press fits may not be ideal as the can have weak attachment.

Figure 11:
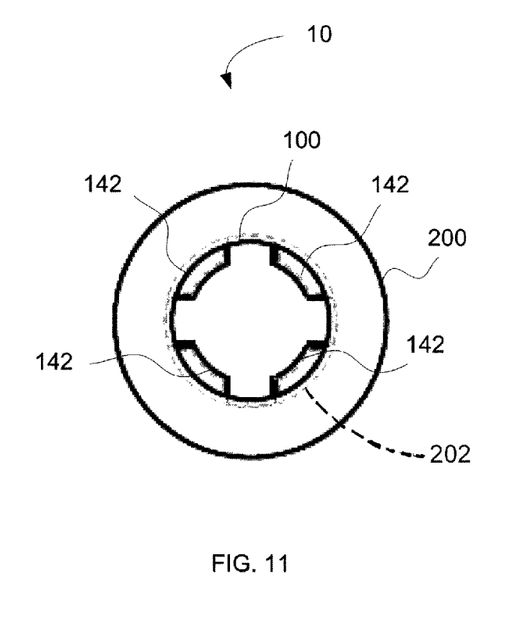
Figure 12:
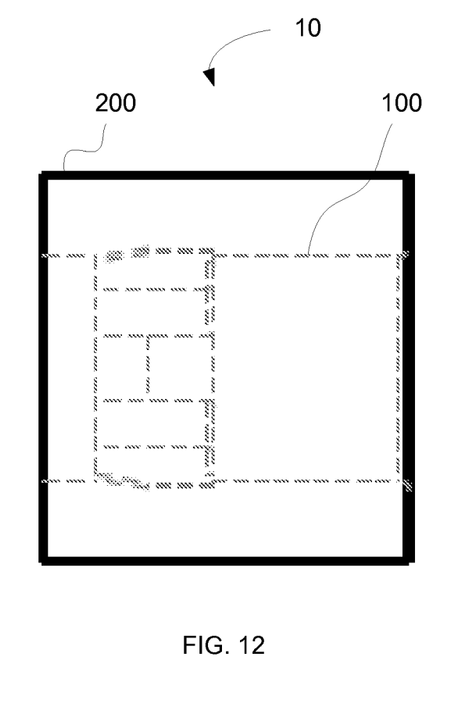
Figure 13:
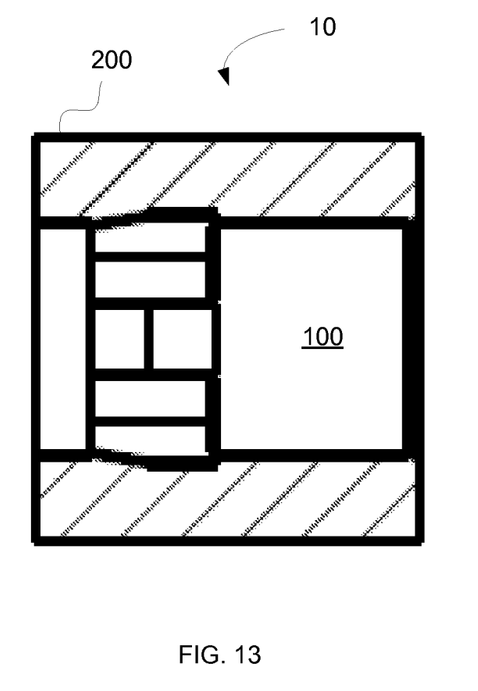

FIG. 11 shows a device 10 that includes an outer component 200 and an inner component 100. The inner component 100 includes inner protrusions 142 on the inner surface. The inner component 100 and the outer component 200 are configured to be locked together. The outer component 200 may include a shoulder 202 within the component configured to prevent the inner component 100 from slipping out of place. Thus, the component 100 is configured to grip a medical device such as a catheter and lock into the outer component 200.

The disclosed device 10 may be made from a stiff yet flexible material. Possible materials include metals such as nitinol, stainless steel, copper, aluminum, nickel, silver, gold, titanium, zinc, etc. Also, the device 10 may use stiff plastics (shore D durometer>=45) including high density polyethylene, polypropylene, ABS, PVC, PEEK, PET, etc. The device 10 may also be made of a combination of metal and plastic material. For example, the body may use one material and the flexible fingers may use a different type of material.

Figure 14:
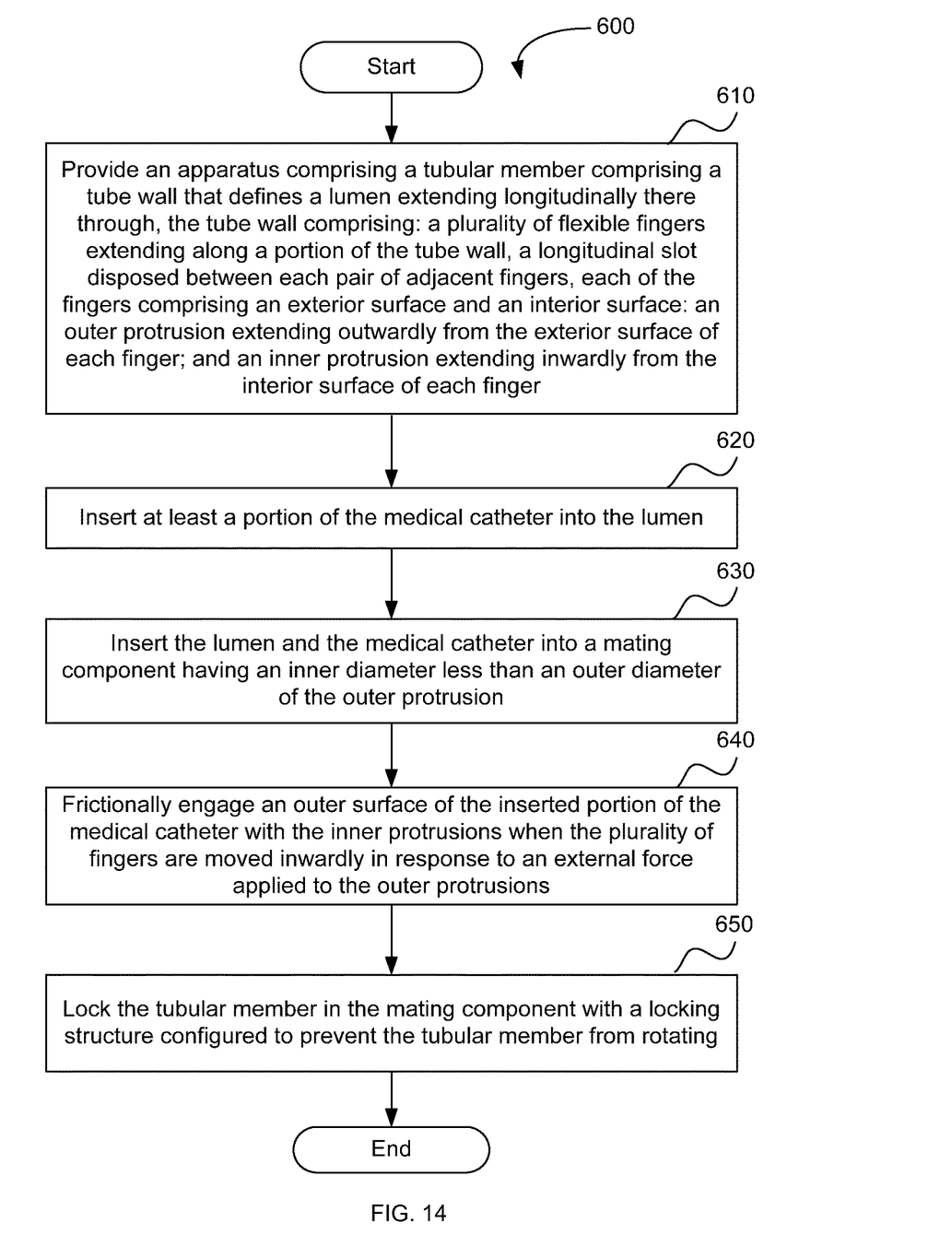
FIG. 14 is a block diagram of a method for securing a medical catheter.

FIG. 14 is a block diagram of a method for securing a medical catheter. In act 610, providing an apparatus including a tubular member comprising a tube wall that defines a lumen extending longitudinally there through. The tube wall includes: a plurality of flexible fingers extending along a portion of the tube wall, a longitudinal slot disposed between each pair of adjacent fingers, each of the fingers comprising an exterior surface and an interior surface. Each finger of the apparatus further includes: an outer protrusions extending outwardly from the exterior surface and an inner protrusions extending inwardly from the interior surface.

In act 620, at least a portion of the medical catheter is inserted into the lumen. This act may be accomplished by an operator or a robot hand controlled by an operator.

In act 630, the lumen and the medical catheter are inserted into a mating component having an inner diameter less than an outer diameter of the outer protrusion. This act may be controlled by an operator or a computer controlled machine.

In act 640, an outer surface of the inserted portion of the medical catheter is frictionally engaged with the plurality of inner protrusions when the plurality of fingers are moved inwardly in response to an external force applied to the plurality of outer protrusions.

In act 650, the tubular member is locked in the mating component with a locking structure configured to prevent the tubular member from rotating. The plurality of outer protrusions may include at least one of the following: a tab, a ridge, a tooth, an arch, or any component protrudes outwards from the outer surface. The plurality of inner protrusion may include at least one of the following: a tab, a ridge, a tooth, an arch, or any component protrudes inwards from the inner surface. The plurality of inner protrusions may include at least two teeth extending perpendicular to the longitudinal slot.

While various embodiments of the invention have been described, it will be apparent to those of ordinary skill in the art that many more embodiments and implementations are possible within the scope of the invention. The different aspects of the described embodiments may be combined together to improve the performance of the catheter apparatus for securing a medical catheter. Accordingly, the invention is not to be restricted except in light of the attached claims and their equivalents. Moreover, the advantages described herein are not necessarily the only advantages of the invention and it is not necessarily expected that every embodiment of the invention will achieve all of the advantaged described.

What is claimed is:

1. An apparatus for securing an elongate medical catheter, comprising:
    a tubular member comprising a tube wall that defines a lumen extending longitudinally there through, the tube wall comprising:
        a plurality of flexible fingers extending along a distal portion of the tube wall, a longitudinal slot disposed between each pair of adjacent fingers and extending to a distal end of the tube wall, each of the fingers comprising an exterior surface and an interior surface, the exterior surface being disposed parallel to a longitudinal axis of the tubular member, an outer protrusion extending outwardly and proximally from the exterior surface of each finger, the outer protrusion being disposed between the longitudinal slots on each side of the finger, the outer protrusion having a proximal portion comprising an interior surface that is spaced apart from the exterior surface of the finger, and a plurality of inner protrusions extending inwardly from the interior surface of each finger, the plurality of inner protrusions being disposed along a longitudinal length of the finger at spaced apart locations,
    wherein the proximal portion of each of the outer protrusions is configured to be compressed inwardly toward the exterior surface of each finger in response to an external force applied to the outer protrusions so as to cause each finger to flex inwardly; and
    wherein the plurality of inner protrusions are configured to frictionally engage an outer surface of the medical catheter disposed within the lumen when the plurality of flexible fingers are moved inwardly in response to the external force applied to the outer protrusions.

2. The apparatus of claim 1, further comprising a mating component having an inner diameter less than an outer diameter of the outer protrusion, the mating component configured to be disposed circumferentially about the tubular member.

3. The apparatus of claim 2, wherein the mating component is configured to apply the external force on the outer protrusions when attached to the tube.

4. The apparatus of claim 1, wherein the mating component comprises a shoulder structure.

5. The apparatus of claim 1, wherein the outer protrusion comprises at least one of the following: a tab, a ridge, a tooth, an arch, or any component protruding outwards from the outer surface of the finger.

6. The apparatus of claim 1, wherein the plurality of inner protrusions each comprise at least one of the following: a tab, a ridge, a tooth, an arch, or any component protruding inwards from the inner surface of the finger.

7. The apparatus of claim 1, wherein the outer protrusion comprises an angled tab extending parallel to the longitudinal slot.

8. The apparatus of claim 1, wherein the plurality of inner protrusions disposed on each finger comprises at least two teeth extending perpendicular to the longitudinal slot.

9. The apparatus of claim 1, wherein the tube wall comprises at least three longitudinal slots and three fingers in the tube wall.

10. The apparatus of claim 1, wherein the lumen has an inner diameter between about 1.0 mm and 20.0 mm.

11. The apparatus of claim 1, wherein the apparatus is made of at least one of metal and plastic material.

12. A method for securing a medical catheter, the method comprising:
    providing an apparatus comprising a tubular member comprising a tube wall that defines a lumen extending longitudinally there through, the tube wall comprising:
        a plurality of flexible fingers extending along a distal portion of the tube wall, a longitudinal slot disposed between each pair of adjacent fingers and extending to a distal end of the tube wall, each of the fingers being disposed parallel to a longitudinal axis of the tubular member and comprising an exterior surface and an interior surface, an outer protrusion extending outwardly from the exterior surface of each finger in a proximal direction away from the distal end of the tube wall, the outer protrusion being disposed between the longitudinal slots on each side of the finger, a proximal end of the outer protrusion comprising an interior surface that is spaced away from the exterior surface of the finger, and a plurality of inner protrusions extending inwardly from the interior surface of each finger, the plurality of inner protrusions being disposed along a longitudinal length of the finger at spaced apart locations;
    inserting at least a portion of the medical catheter into the lumen of the tubular member;
    inserting the tubular member and the medical catheter into a mating component having an inner diameter less than an outer diameter of the outer protrusion so as to compress the proximal portion of each of the outer protrusions inwardly toward the exterior surface of each finger and thereby cause each finger to flex inwardly; and
    frictionally engaging an outer surface of the inserted portion of the medical catheter with the plurality of inner protrusions when the plurality of flexible fingers are moved inwardly in response to an external force applied by the mating component to the outer protrusions.

13. The method of claim 12, further comprising the step of locking the tubular member into the mating component with a shoulder structure configured to prevent the tubular member from rotating.

14. The method of claim 13, wherein the outer protrusion comprises at least one of the following: a tab, a ridge, a tooth, an arch, or any component protruding outwards from the outer surface of the finger.

15. The method of claim 12, wherein the plurality of inner protrusions each comprise at least one of the following: a tab, a ridge, a tooth, an arch, or any component protruding inwards from the inner surface of the finger.

16. The method of claim 12, wherein the plurality of inner protrusions disposed on each finger comprises at least two teeth extending perpendicular to the longitudinal slot.

17. An apparatus for securing a medical catheter, the apparatus comprising:
   a tubular member comprising a tube wall that defines a lumen extending longitudinally there through, the tube wall comprising:
      a plurality of flexible fingers extending parallel to each other and along a portion of the tube wall, the flexible fingers each having a free end that is defined by a distal end of the tube wall, a longitudinal slot disposed between each pair of adjacent fingers to permit the free ends of the fingers to move radially, each of the fingers comprising an exterior surface and an interior surface, an outer protrusion extending outwardly from the exterior surface of each finger, the outer protrusion being disposed between the longitudinal slots on each side of the finger, the outer protrusion having a proximal end comprising an interior surface that is spaced outwardly and apart from the exterior surface of the finger, and a plurality of inner protrusions extending inwardly from the interior surface of each finger, the plurality of inner protrusions being disposed along a longitudinal length of the finger at spaced apart locations; and
   a mating component having an inner diameter less than an outer diameter of the outer protrusion, the mating component being configured to be disposed circumferentially about the tubular member and engage the outer protrusions,
   wherein the proximal end of each of the outer protrusions is configured to be compressed inwardly toward the exterior surface of each finger in response to an external force applied to the outer protrusions so as to cause each finger to flex inwardly; and
   wherein the plurality of inner protrusions are configured to frictionally engage an outer surface of the medical catheter disposed within the lumen when the mating component applies the external force to the outer protrusions so as to move the flexible fingers inwardly.

18. The apparatus of claim 17, wherein the mating component comprises a shoulder structure configured to prevent the first component from rotating.

19. The apparatus of claim 17, wherein the outer protrusion on each finger comprises at least one of the following: a tab, a ridge, a tooth, an arch, or any structure extending outwardly from the outer surface of the finger.

* * * * *